US008357808B2

(12) United States Patent
Koyama et al.

(10) Patent No.: US 8,357,808 B2
(45) Date of Patent: Jan. 22, 2013

(54) PROCESS FOR PRODUCING DIAMINE DERIVATIVE

(75) Inventors: Takeo Koyama, Hiratsuka (JP); Satoshi Kondo, Hiratsuka (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/228,928

(22) Filed: Sep. 9, 2011

(65) Prior Publication Data

US 2012/0041206 A1 Feb. 16, 2012

Related U.S. Application Data

(63) Continuation of application No. PCT/JP2010/053905, filed on Mar. 9, 2010.

(30) Foreign Application Priority Data

Mar. 10, 2009 (JP) .................................. 2009-057031

(51) Int. Cl.
C07D 213/72 (2006.01)
(52) U.S. Cl. ...................................................... 546/304
(58) Field of Classification Search ........................ None
See application file for complete search history.

(56) References Cited

U.S. PATENT DOCUMENTS

| | | | |
|---|---|---|---|
| 5,055,600 | A | 10/1991 | Wagner |
| 5,149,855 | A | 9/1992 | Sakimae et al. |
| 5,677,469 | A | 10/1997 | van Eikeren et al. |
| 7,192,968 | B2 | 3/2007 | Yoshino et al. |
| 7,342,014 | B2 | 3/2008 | Ohta et al. |
| 7,365,205 | B2 | 4/2008 | Ohta et al. |
| 7,576,135 | B2 | 8/2009 | Ohta et al. |
| 7,674,904 | B2 | 3/2010 | Doshan et al. |
| 2004/0122063 | A1 | 6/2004 | Yoshino et al. |
| 2005/0020645 | A1 | 1/2005 | Ohta et al. |
| 2005/0119486 | A1 | 6/2005 | Ohta et al. |
| 2005/0245565 | A1 | 11/2005 | Ohta et al. |
| 2006/0252837 | A1 | 11/2006 | Ohta et al. |
| 2006/0275357 | A1 | 12/2006 | Oomura et al. |
| 2007/0135476 | A1 | 6/2007 | Nagasawa et al. |
| 2008/0015215 | A1 | 1/2008 | Ohta et al. |
| 2009/0105491 | A1 | 4/2009 | Sato et al. |
| 2009/0192313 | A1 | 7/2009 | Nagasawa et al. |
| 2009/0270446 | A1 | 10/2009 | Ohta et al. |
| 2009/0281074 | A1 | 11/2009 | Ohta et al. |
| 2010/0081685 | A1 | 4/2010 | Kojima et al. |
| 2011/0275821 | A1* | 11/2011 | Koyama .......................... 546/114 |

FOREIGN PATENT DOCUMENTS

| | | |
|---|---|---|
| JP | 4-227629 | 8/1992 |
| JP | 11-180899 | 7/1999 |
| JP | 2000-344735 | 12/2000 |
| JP | 2001-151724 | 6/2001 |
| JP | 2008-542287 | 11/2008 |
| WO | WO 01/74774 | 10/2001 |
| WO | WO 03/000657 | 1/2003 |
| WO | WO 03/000680 | 1/2003 |
| WO | WO 03/016302 | 2/2003 |
| WO | WO 2004/058715 | 7/2004 |
| WO | WO 2005/047296 | 5/2005 |
| WO | WO 2007/032498 | 3/2007 |
| WO | WO 2008/043996 | 4/2008 |
| WO | WO 2008/129846 | 10/2008 |
| WO | WO 2008/156159 | 12/2008 |

OTHER PUBLICATIONS

U.S. Appl. No. 13/157,590, filed Jun. 10, 2011, Koji Sato.
U.S. Appl. No. 13/162,922, filed Jun. 17, 2011, Takeo Koyama.
U.S. Appl. No. 13/163,287, filed Jun. 17, 2011, Takashi Abiko.
U.S. Appl. No. 13/181,596, filed Jul. 13, 2011, Makoto Ono.
U.S. Appl. No. 13/273,360, filed Oct. 14, 2011, Toshiharu Yoshino.
U.S. Appl. No. 13/328,847, filed Dec. 16, 2011, Makoto Kamada.
U.S. Appl. No. 13/231,081, filed Sep. 13, 2011, Koutarou Kawanami.
PCT International Preliminary Report on Patentability of Int'l App. No. PCT/JP2010/053905 dated Oct. 18, 2011, 5 pages.
International Search Report of Int'l App. No. PCT/JP2010/053905 dated Apr. 21, 2010, 2 pages.
English Translation of PCT Written Opinion of the International Searching Authority of Int'l App. No. PCT/JP2010/053905 dated May 11, 2010, 4 pages.
PCT International Preliminary Report on Patentability of Int'l App. No. PCT/JP2010/053976 dated Oct. 18, 2011, 5 pages.
International Search Report of Int'l App. No. PCT/JP2010/053976 dated Apr. 13, 2010, 2 pages.
English Translation of PCT Written Opinion of the International Searching Authority of Int'l App. No. PCT/JP2010/053976 dated Apr. 13, 2010, 4 pages.
Dubois, D., et al., "Clinical calorimetry. X. A formula to estimate the approximate surface area if the height and weight be known" *Archives of Internal Medicine*, 17, 863-71 (1916).
Elodi, S., et al., "Optimization of conditions for the catalytic effect of the factor IXa-factor VIII complex: probable role of the complex in the amplification of blood coagulation" *Thrombosis Research*, 15(5-6), 617-29 (1979).
Fujimoto, et al., "Studies on the physical surface area of Japanese: Part 18 calculation formulas in three stages over all age" *Japanese Journal of Hygene*, vol. 23(5): 443-450 (1968)—(Contains an English Abstract).

(Continued)

*Primary Examiner* — Janet Andres
*Assistant Examiner* — Heidi Reese
(74) *Attorney, Agent, or Firm* — Locke Lord, LLP (57) ABSTRACT

The problem to be solved is to provide an important intermediate for production of an FXa inhibitor. The solution thereto is a process for industrially producing a compound (1) represented by the following formula (1):

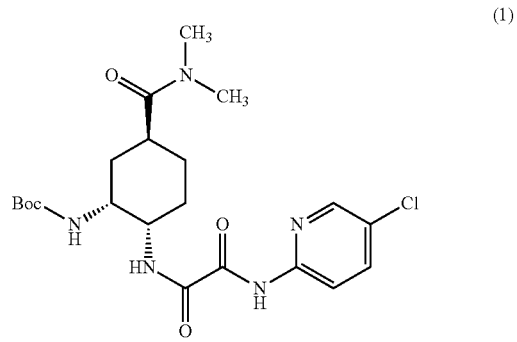

wherein Boc represents a tert-butoxycarbonyl group.

18 Claims, 2 Drawing Sheets

OTHER PUBLICATIONS

Furugohri, T., et al., "DU-176b, A potent and orally active factor Xa inhibitor: In vitro and in vivo pharmacological profiles" *Journal of Thrombosis and Haemostasis*, 6(9), 1542-1549 (2008).

Goldberg, SI, et al., "Correlation of configuration and rotatory direction for several 4-substituted cyclohexenes" *Journal of Organic Chemistry*, 31:240-243 (1966).

Hylek, E.M., "Drug evaluation: DU-176b, an oral, direct Factor Xa antagonist." Current Opinion in Investigational Drugs, 8, (9), 778-783 (2007).

Johansson, LC, et al., "Comparison of the Pharmacokinetics and Pharacodynamics of Ximelagatran in young and elderly, healthy Japanese men" *Blood* 100, 3980 (2002).

Mendell, J., et al., "The pharmacokinetics and pharmacodynamics of the direct factor Xa inhibitor, edoxaban co-administered with digoxin: a randomized, open-label, dual treatment sequence, parallel-group study" *Journal of Clinical Pharmacology*, 49(9), 1125 (2009).

Mendell, J., et al., "Thorough QT/QTC study with edoxaban to evaluate effect of therapeutic and supratherapeutic exposure on QTC interval duration in healthy subjects" *Journal of Clinical pharmacology* 49(9), 1122 (2009).

Mould, D., et al., "A population pharmacokinetic pharmacodynamic and logistic regression analysis of lotrafiban in patients" *Clinical Pharmacology and Therapeutics* 69(4), 210-222 (2001).

Mueck, W., et al., "Population pharmacokinetics and pharmacodynamic of rivaroxaban—an oral, direct factor Xa inhibitor—in patients undergoing major orthopaedic surgery" *Clinical Pharmacokinetics*, 47(3), 203-216 (2008).

Nohira, H. "4 Diastereomer Method", Edited by CSJ: The Chemical Society of Japan, kogaku Iseitai no Bunri Kikan Kagaku Sosetsu No. 6, 3rd edition, Japan Scientific Societies Press, pp. 45 to 54, (1999).

Product Information, Clexane® and Clexane® Forte, Clexane® PI MKT, #6178v16, pp. 1-19 (2008).

Ridout, G., et al., "Effect of renal function on edoxaban pharmacokinetics (PK) and on population PK/PK-PD model" *Journal of Clinical Pharmcology* 49(9), 1124 (2009).

Schwartz, HM, et al., "Predicting the Enantiomeric Selectivity of Chymotrypsin. Homologous Series of Ester Substrates" *J. Am. Chem. Soc.*, 100, 5199-5203, (1978).

Sixma JJ, et al., "The ideal anti-thrombotic drug" *Thrombosis research*, 68(6), 507-12 (1992).

Takahashi, H. "3.Warfarin Oto no kojinsa" *Kessen to Junkan*, 14(3), 198-202 (2006) (English Translation Provided).

Tanyeli, C, et al., "Enzyme catalyzed reverse enantiomeric separation of methyl (±)-3-cyclohexene-1-carboxylate" *Tetrahedron: Asymmetry*, 15, 2057-2060, (2004).

Trost, BM, et al., "An Asymmetric Synthesis of (+)-Phyllanthoci" Tetrahedron Lett., 32, 1613-1616, (1991).

Vene, N., et al., "High D-dimer levels predict cardiovascular events in patients with chronic atrial fibrillation during oral anticoagulant therapy" *Thrombosis and Haemostasis*, 90(6), 1163-1172 (2003).

International Preliminary Report on Patentability, issued in PCT/JP2009/070613, mailed Jul. 5, 2011.

International Search Report, issued in PCT/JP2009/070613, mailed Feb. 16, 2010.

Written Opinion of the International Searching Authority, issued in PCT/JP2009/070613, mailed Jul. 5, 2011.

International Preliminary Report on Patentability, issued in PCT/JP2009/070874, mailed Jul. 5, 2011.

International Search Report, issued in PCT/JP2009/070874, mailed Mar. 23, 2010.

Written Opinion of the International Searching Authority, issued in PCT/JP2009/070874, mailed Jul. 5, 2011.

International Preliminary Report on Patentability, issued in PCT/JP2009/071016, mailed Jul. 5, 2011.

International Search Report, issued in PCT/JP2009/071016, mailed Feb. 16, 2010.

Written Opinion of the International Searching Authority, issued in PCT/JP2009/071016, mailed Jul. 5, 2011.

International Preliminary Report on Patentability, issued in PCT/JP2010/050128, mailed Aug. 16, 2011.

International Search Report, issued in PCT/JP2010/050128, mailed Apr. 6, 2010.

Written Opinion of the International Searching Authority, issued in PCT/JP2010/050128, mailed Aug. 16, 2011.

International Preliminary Report on Patentability, issued in PCT/JP2010/057990, mailed Dec. 12, 2011.

International Search Report, issued in PCT/JP2010/057990, mailed Jun. 8, 2010.

Written Opinion of the International Searching Authority, issued in PCT/JP2010/057990, mailed Dec. 12, 2011.

International Preliminary Report on Patentability, issued in PCT/JP2010/060261, mailed Dec. 20, 2011.

International Search Report, issued in PCT/JP2010/060261, mailed Sep. 21, 2010.

Written Opinion of the International Searching Authority, issued in PCT/JP2010/060261, mailed Dec. 20, 2011.

Patani, et al., "Bioisosterism: A rational approach in drug design", Chem. Rev. 1996, 3147-3176.

Supplementary European Search Report mailed Jun. 4, 2012 in EP Application No. 09 83 3467, which corresponds to related U.S. Appl. No. 13/163,287.

Supplementary European Search Report mailed Aug. 30, 2012 in EP Application No. 10769172.0, which corresponds to related U.S. Appl. No. 13/266,967.

Furugohri, T, et al, "Pharmaceutical Characterization, Antithromboti and Bleeding Effects of DU-176b", Journal of Thrombosis and Haemostasis, 3(supp. 1), Abstract P1110, (2005).

Zafar, Um, et al., "Antithrombotic effects of factor Xa inhibition with DU-176b: Phase-I study of an oral, direct factor Xa inhibitor using an ex-vivo flow chamber", Thrombosis and Haemostasis, 98(4):833-888 (2007).

Walker, MB, "Understanding the PT-INR Test", obtained from the internet www.vclotacare.com/ptinr.aspx (retrieved Apr. 24, 2012).

Anonymous, "A phase 2, randomized, parallel group, multi-center, multi-national study for the evaluation of safety and efficacy of two fixed dosages of DU-176b in subjects with non-valvular atrial fibrillation", Clinical Trials.gov NCT00806624 obtained from the internet clinicaltrials.gov/archive/NCT00806624/2008_12_10 (retrieved Apr. 23, 2012).

Kozma, D., "CRC Handbook of Optical Resolutions Via Diastereomeric Salt Formation", CRC Press: Washington, DC, Chapters 4, 5, and 6 (2002).

Murakami, "Asymmetric Transformation of a Racemic a-(Phthalimidooxy)arylacetic Ester by a Combination of Preferential Crystallization and Simultaneous Racemization" *Chirality*5 141-48 (1993).

Allan, R., "Synthesis of analogs of GABA. VI. Stereoisomers of cis-3-aminocyclohexanecarboxylic acid" *Australian Journal of Chemistry*, 34(10):2231-36 (Abstract only).

Chiappe, et al. "Nucleophilic Displacement Reactions in Ionic Liquids: Substrate and Solvent Effect in the Reaction of $NaN_3$ and KCN with Alkyl Halides and Tosylates," *Journal of Organic Chemistry*68:6710-15 (2003).

Betti, C., et al. "Reactivity of anionic nucleophiles in ionic liquids and molecular solvents," *Tetrahedron*64:1689 (2008).

Thomas, M., et al, "Management of Venous Thromboembolism", *Arch Intern Med.*, 163:759-768 (2003).

Turpie, Agg., "Oral, direct factor Xa inhibitors in development for the prevention and treatment of thromboembolic diseases", *Arteriosclerosis, Thrombosis, and Vascular Biology*, 27:1238-1247 (2007).

De Caterina, R, et al. "Anticoagulants in heart disease: current status and perspectives", *European Heart Journal*28:880-913 (2007).

Dyke, CK., "First experience with direct factor Xa inhibition in patients with stable coronary disease: a pharmacokinetic and pharmacodynamics evaluation", *Circulation.*, 105:2385-2391 (2002).

Iba, T., et al., "Factor Xa-inhibitor (DX-9065a) modulates the leukocyte-endothelial cell interaction in endotoxemic rat", *Shock.*, 17(2):159-162 (2002).

Blagden, N., et al. "Crystal engineering of active pharmaceutical ingredients to improve solubility and dissolution rates." Advanced Drug Delivery Reviews, 59:603-616 (2007).

Ohta, T., et al. "Preparation of N,N'-bis(heterocyclic acyl)cycloalkanediamine and heterocyclediamine derivatives as inhibitors of activated blood coagulation factor X (factor Xa)", Hcaplus 2003:5928 (2003).

Serajuddin, A., "Salt formation to improve drug solubility." Advanced Drug Delivery Reviews, 59:617-630 (2007).

* cited by examiner

PROCESS FOR PRODUCING DIAMINE DERIVATIVE

This application is a continuation of International Application No. PCT/JP2010/053905, filed on Mar. 9, 2010, entitled "PROCESS FOR PRODUCING DIAMINE DERIVATIVE", which claims the benefit of Japanese Patent Application Number JP 2009-057031, filed on Mar. 10, 2009, all of which are hereby incorporated by reference.

FIELD OF THE INVENTION

The present invention relates to a process for industrially producing an optically active diamine derivative that is important for production of a compound (A) as an activated blood coagulation factor X (FXa) inhibitor or a pharmacologically acceptable salt thereof, or a hydrate thereof.

BACKGROUND OF THE INVENTION

Compound (A) represented by the following formula or a pharmacologically acceptable salt thereof, or a hydrate thereof is a compound that exhibits an FXa inhibitory effect, as disclosed in Patent Literatures 1 to 3, and is useful as preventive and/or therapeutic drugs for thrombotic and/or embolic diseases.

(A)

A compound (1), an optically active diamine derivative, described in the scheme shown below is known as an intermediate for the production of compound (A) as an FXa inhibitor or a pharmacologically acceptable salt thereof, or a hydrate thereof. The pamphlet of International Publication No. WO 2007/032498 (JP 2007-106759) discloses a process for producing compound (1), comprising adding a compound (3) to an excessive amount of a tertiary amine to neutralize the salt and then adding a compound (2) to the mixture [Scheme A].

wherein Boc represents a tert-butoxycarbonyl group.

Citation List

Patent Literatures

Patent Literature 1: International Publication No. WO 2004/058715
Patent Literature 2: International Publication No. WO 2003/016302
Patent Literature 3: International Publication No. WO 2003/000680
Patent Literature 4: International Publication No. WO 2007/032498 (JP 2007-106759)

SUMMARY OF INVENTION

Technical Problem

The production process disclosed in the pamphlet of International Publication No. WO 2007/032498 (JP 2007-106759) has been found to deposit a gel of a compound (3a) (obtained by the neutralization of compound (3) with the tertiary amine), which then hardens and solidifies the reaction system and makes stirring difficult. As a result, it has been demonstrated that, disadvantageously, reaction yields are drastically reduced due to the increased formation of by-products. Furthermore, it has also been demonstrated that the prevention of such solidification is exceedingly difficult.

Thus, an object of the present invention is to solve these problems and to provide a novel process for industrially producing compound (1) that is an important synthetic intermediate for production of compound (A).

The present inventors have conducted diligent studies with the aim of avoiding the drastic reduction in yield caused by solidification of the reaction system, which is a problem in the conventional process for producing compound (1), and obtaining a novel process for industrially producing compound (1).

As a result of studies over the years, the present inventors have completed the present invention by finding that: the order of addition is important in which compound (2) is first treated with the tertiary amine and subsequently, compound (3) is added thereto; and an effective process involves adding the tertiary amine in divided portions to prevent decomposition of the free form of compound (2).

Solution to Problem

The present invention provides (1) to (21) shown below.
(1) A process for producing a compound (1) represented by the following formula:

(1)

wherein Boc represents a tert-butoxycarbonyl group, the process comprising:
[Step 1]: treating a compound (2) represented by the following formula:

(2)

With a tertiary amine in a C2-C4 nitrile solvent; and
[Step 2]: then adding, to the mixed solution of [Step 1], a compound (3) represented by the following formula:

(3)

wherein Boc is as defined above.
(2) The production process according to (1), wherein the C2-C4 nitrile solvent is acetonitrile.
(3) The production process according to (1) or (2), wherein the amount of compound (2) is stoichiometrically 1.10 to 1.27 molar equivalents with respect to compound (3).
(4) The production process according to any one of (1) to (3), wherein the tertiary amine is one or two or more selected from the group consisting of tri(C1-C4 alkyl)amines, 1-(C1-C3 alkyl)piperidine, and 4-(C1-C3 alkyl)morpholine.
(5) The production process according to any one of (1) to (3), wherein the tertiary amine is one or two or more selected from tri(C1-C4 alkyl)amines.
(6) The production process according to any one of (1) to (3), wherein the tertiary amine is triethylamine.
(7) The production process according to any one of (1) to (6), wherein [Step 1] comprises adding compound (2) represented by the following formula:

(2)

into the C2-C4 nitrile solvent and subsequently adding the tertiary amine thereto.
(8) The production process according to any one of (1) to (6), wherein [Step 1] comprises adding the tertiary amine into the C2-C4 nitrile solvent and subsequently adding thereto compound (2) represented by the following formula:

(2)

(9) The production process according to (7) or (8), wherein the addition of compound (2) or the tertiary amine is performed at 45° C. or lower.
(10) The production process according to (7) or (8), wherein the addition of compound (2) or the tertiary amine is performed in the range of 0 to 35° C.
(11) The production process according to any one of (1) to (10), wherein the amount of the tertiary amine added in [Step 1] is stoichiometrically 0.87 to 1.08 molar equivalents with respect to compound (2).
(12) The production process according to any one of (1) to (11), further comprising adding an additional tertiary amine after the procedure of [Step 2].
(13) The production process according to (12), wherein the amount of the additional tertiary amine added is stoichiometrically in the range of 3.02 to 4.53 molar equivalents with respect to compound (2).
(14) The production process according to (12) or (13), wherein the addition of the additional tertiary amine is performed at 50 to 65° C.
(15) The production process according to any one of (12) to (14), further comprising stirring the reaction mixture at 60 to 80° C. after the addition of the additional tertiary amine.
(16) The production process according to (15), wherein the stirring time is 6 hours or longer.
(17) The production process according to (15), wherein the stirring time is in the range of 6 to 24 hours.

(18) A process for producing a compound (1) represented by the following formula:

(1)

wherein Boc represents a tert-butoxycarbonyl group, the process comprising:

[Step 1]: treating a compound (2) represented by the following formula:

(2)

with triethylamine at stoichiometrically 0.87 to 1.08 molar equivalents with respect to compound (2) in acetonitrile;

[Step 2]: then adding, to the mixed solution of [Step 1], a compound (3) represented by the following formula:

(3)

wherein Boc is as defined above,
then adding an additional tertiary amine at stoichiometrically 3.23 to 4.32 molar equivalents with respect to compound (2) at 50 to 65° C., and stirring the reaction mixture at 60 to 80° C. for 6 hours or longer.

(19) The process for producing compound (1) represented by the following formula according to (1):

(1)

wherein Boc represents a tert-butoxycarbonyl group, wherein compound (1) is used as a synthetic intermediate for production of a compound (A-a) represented by the following formula:

(A-a)

(20) A process for producing a compound (A-a) represented by the following formula:

(A-a)

comprising using a compound (1) produced by a production process according to (1).

(21) A process for producing a compound (A-a) represented by the following formula:

(A-a)

comprising using a compound (1) produced by a production process according to (1), the process comprising the steps of:

deprotecting a Boc group in compound (1) represented by the following formula:

(1)

wherein Boc represents a tert-butoxycarbonyl group, to obtain a compound (7) represented by the following formula or a salt thereof:

(7)

condensing compound (7) with a compound (8) represented by the following formula:

(8)

to obtain a compound (A) represented by the following formula:

(A)

and
treating compound (A) with p-toluenesulfonic acid or a hydrate thereof to obtain compound (A-a).

ADVANTAGEOUS EFFECTS OF INVENTION

According to the present invention, compound (1) that is an intermediate for production of compound (A) useful as an FXa inhibitor can be produced at stable yields as high as 93 to 95% by avoiding a reduction in reaction yield caused by solidification of the reaction system, which is a problem of the conventional process. Thus, the production process of the present invention is useful as a process for producing compound (A) useful as an FXa inhibitor.

DETAILED DESCRIPTION

Hereinafter, the present invention will be described in detail.

The specific "FXa inhibitor" according to the present specification is preferably, for example, compound (A) described above. Compound (A) may be a free form (free base) or a hydrate thereof or may be a pharmacologically acceptable salt or a hydrate of the salt.

Examples of the pharmacologically acceptable salt of compound (A) include hydrochloride, sulfate, hydrobromide, hydroiodide, phosphate, nitrate, benzoate, methanesulfonate, 2-hydroxyethanesulfonate, p-toluenesulfonate, acetate, propanoate, oxalate, malonate, succinate, glutarate, adipate, tartrate, maleate, fumarate, malate, and mandelate.

The salt of compound (A) is preferably hydrochloride or p-toluenesulfonate, particularly preferably p-toluenesulfonate.

Compound (A) or a salt thereof, or a hydrate thereof is preferably
$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide;
$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide hydrochloride;
$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide mono-p-toluenesulfonate; or
$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide mono-p-toluenesulfonate monohydrate, particularly preferably
$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide mono-p-toluenesulfonate monohydrate (A-a).

(A-a)

Hereinafter, the production process of the present invention will be described in detail.

The optically active amide derivative compound (1) of the present invention can be produced by performing the procedures of [Step 1] and [Step 2] in the order as shown in the following scheme:

wherein Boc represents a tert-butoxycarbonyl group.

[Step 1]: the step of treating compound (2) represented by the following formula:

With a tertiary amine in a C2-C4 nitrile solvent is performed, and then

[Step 2]: compound (3) represented by the following formula:

wherein Boc is as defined above, is added to the mixed solution of [Step 1] to produce compound (1).

Examples of the C2-C4 nitrile solvent used in the [Step 1] can include acetonitrile, propionitrile, and butyronitrile. Among them, the reaction solvent is preferably acetonitrile.

Organo-tertiary bases generally used can be used as the tertiary amine according to the present invention. Examples thereof can include alkylamines comprising identical or different C1 to C8 alkyls, 1-(C1-C3 alkyl)pyrrolidine, 1-(C1-C3 alkyl)piperidine, 4-(C1-C3 alkyl)morpholine, 1,8-diazabicyclo[5.4.0]undec-7-ene (DBU), 1,5-diazabicyclo[4.3.0]non-5-ene (DBN), di(C1-C3 alkyl)aniline, and 4-di(C1-C3 alkyl)aminopyridine. Among these, the tertiary amine is preferably trimethylamine, triethylamine, ethyl(diisopropyl)amine, 1-methylpiperidine, 1-ethylpiperidine, 4-methylmorpholine, N,N-dimethylaniline, or N,N-diethylaniline, or the like.

Hereinafter, [Step 1] and [Step 2] performed subsequently thereto will be described in detail.

[Step 1] is the step of treating compound (2) with a tertiary amine in a C2-C4 nitrile solvent to prepare a neutralized compound (2a) represented by the following formula:

More specific examples of preferable aspects of [Step 1] can include [Step 1 (Method A)] to [Step 1 (Method C)] shown below.

[Step 1 (Method A)]: "adding compound (2) into a C2-C4 nitrile solvent and then adding a tertiary amine thereto at 45° C. or lower".

The amount of the C2-C4 nitrile solvent is preferably in a range of 4 to 6 parts by volume with respect to 1 part by weight of compound (3). The amount of compound (2) used is stoichiometrically preferably 1.1 to 1.3 molar equivalents, more preferably approximately 1.2 molar equivalents, with respect to compound (3). The temperature of the reaction solution is preferably 45° C. or lower, more preferably in a range of 0 to 35° C. The tertiary amine used can be those exemplified above and is preferably triethylamine. The amount of the tertiary amine added is stoichiometrically preferably 0.87 to 1.08 molar equivalents, more preferably approximately 0.98 molar equivalent, with respect to compound (2).

[Step 1 (Method B)]: "adding a tertiary amine into a C2-C4 nitrile solvent and then adding compound (2) thereto at 45° C. or lower".

The amount of the C2-C4 nitrile solvent, the amount of compound (2) used, the temperature of the reaction solution, the tertiary amine used, the amount of the tertiary amine added, and the temperature at which the tertiary amine or the compound (2) is added are the same as in Method A.

[Step 1 (Method C)]: "adding compound (2) into a C2-C4 nitrile solvent, then heating the mixture to a range of 50 to 65° C., and adding a tertiary amine thereto".

The amount of the C2-C4 nitrile solvent, the amount of compound (2) used, and the tertiary amine used are the same as in Method A. The amount of the tertiary amine added is stoichiometrically preferably 3.2 molar equivalents or more, more preferably in the range of 4.9 to 6.5 molar equivalents, with respect to compound (3). Method C is free from addition of an additional tertiary amine after [Step 2].

Among Methods A to C, Methods A and B are preferable.

[Step 2] in the present invention is the step of adding, to the mixed solution of [Step 1], compound (3) represented by the following formula:

(3)

wherein Boc represents a tert-butoxycarbonyl group.

In this context, when Method C is adopted, the shorter the interval from completion of the addition of the tertiary amine to initiation of the addition of compound (3) is, the more greatly reduction in the yield of compound (1) caused by solidification of the reaction solution can be avoided. The point in time when the addition of compound (3) is initiated in Method C is preferably within 15 minutes after the addition of the tertiary amine, more preferably at the completion of the addition of the tertiary amine, even more preferably concurrently with the addition of the tertiary amine at the point in time when the addition of ⅕ or more of the total amount of the tertiary amines added has been completed.

When Method A or B is adopted, an additional tertiary amine is added to the mixed solution of [Step 2] with the internal temperature of the mixed solution set to 50 to 65° C., and then, the reaction mixture is stirred at 60 to 80° C.

After the completion of the reaction, the reaction mixture is cooled, and water is added thereto for crystallization. The resulting crystals are collected to obtain compound (1).

The amount of the additional tertiary amine added in Methods A and B is stoichiometrically preferably in the range of 3.23 to 4.32 molar equivalents with respect to compound (2) [the total amount of the tertiary amines added is stoichiometrically 4.9 to 6.5 molar equivalents with respect to compound (3)].

This addition of the additional tertiary amine converts compound (3) which is an oxalate to compound (3a) which is a free base (free form).

wherein Boc represents a tert-butoxycarbonyl group.

After the addition of the additional tertiary amine, the reaction mixture is stirred at 60 to 80° C. In this context, the stirring time is preferably 6 hours or longer, more preferably approximately 6 to 24 hours. Moreover, the endpoint of the reaction may be determined by confirming the sample in the reaction solution using equipment of HPLC or the like.

In the present invention, Method A is particularly preferable. A specific aspect of the production of the compound (1) using Method A is as follows:

Compound (2) is added to acetonitrile, and triethylamine is added thereto at stoichiometrically 0.87 to 1.08 molar equivalents with respect to compound (2). To the mixed solution, compound (3) is then added. To the reaction mixture, additional tertiary amine is subsequently added at stoichiometrically 3.23 to 4.32 molar equivalents with respect to compound (2) at 50 to 65° C., and the mixture is stirred at 60 to 80° C. for 6 hours or longer to produce compound (1).

After the completion of the reaction, the compound (1) is isolated and purified. Next, the procedure of isolating compound (1) as crystals will be described.

The reaction mixture is cooled. Water is added thereto, and the mixture is stirred to complete crystallization. In this context, the cooling of the reaction mixture is performed preferably at 0 to 60° C., more preferably 0 to 50° C. The amount of water added is preferably in the range of 6 to 11 parts by volume with respect to 1 part by weight of the compound (3) [6 to 11 (v/w)].

The procedure of obtaining crystals of compound (1) after the crystallization is performed such that the precipitated crystals are cooled to complete crystallization, and the resulting crystals are collected by filtration, washed with water, and then dried. In this context, the procedure of obtaining the precipitated crystals can be performed by collecting the crystals by filtration under normal pressure or reduced pressure. The crystallization temperature is preferably −10 to 35° C. The amount of water for washing the crystals is preferably approximately 5 parts by volume with respect to 1 part by weight of the compound (3) [5 (v/w)].

Compound (2) used in [Step 1] can be produced as shown below. Specific examples of the production can include a process described in Reference Example 2. Specifically, compound (2) can be produced by adding a commercially available aniline derivative compound (2b) and a compound (2c) into a C2-C4 nitrile solvent with stirring.

Examples of the C2-C4 nitrile solvent used in this reaction can include acetonitrile, propionitrile, and butyronitrile. Acetonitrile is preferable. The amount of the solvent used is preferably in the range of 10 to 17 parts by volume with respect to 1 part by weight of compound (2b) [10 to 17 (v/w)]. The amount of the compound (2c) used is stoichiometrically preferably in the range of 1.06 to 1.21 molar equivalents with respect to the compound (2b). The reaction temperature is preferably in the range of 40 to 80° C. The reaction time is preferably 1 hour longer, more preferably approximately 1 to 7 hours. Compound (2) thus produced can be isolated by allowing compound (2) to crystallize and collecting the crystals by filtration. The crystallization temperature is preferably in the range of −25 to 35° C. The crystals of compound (2) can be isolated by collection by filtration. When compound (2) is then used in [Step 1], compound (2) collected by filtration may be used in a dry state (dry form) after drying under normal pressure or reduced pressure or may be used in a wet state (wet form).

A known process disclosed in Patent Literature 1 or 3 may be used as a process for producing compound (A) useful as an FXa inhibitor or compound (A-a) (mono-p-toluenesulfonate monohydrate of compound (A)) using compound (1) of the present invention. Specifically, these compounds can be produced as shown in the following scheme and Reference Examples 4 and 5 described later:

(A)

(A)

(A-a)

wherein Boc represents a tert-butoxycarbonyl group.

EXAMPLES

Next, the present invention will be described in detail with reference to the Examples. However, the present invention is not intended to be limited to these in any way.

Tetramethylsilane was used as the internal standard for the nuclear magnetic resonance (NMR) spectra. Abbreviations showing multiplicity represent s=singlet, d=doublet, t=triplet, q=quartet, m=multiplet, and brs=broad singlet.

Reference Example 1

Tert-butyl (1R,2S,5S)-2-amino-5-(dimethylaminocarbonyl)cyclohexylcarbamate monooxalate (3)

(3)

wherein Boc represents a tert-butoxycarbonyl group.

[Step 1] Synthesis of tert-butyl {(1R,2R,5S)-5-[(dimethylamino)]-2-hydroxycyclohexylcarbonyl}carbamate (4)

(4)

wherein Boc is as defined above.

A 28% aqueous ammonia solution (5 ml) was added to (1S,3S,6R)-N,N-dimethyl-7-oxabicyclo[4.1.0]heptane-3-carboxamide (1 g) at room temperature. After stirring at 40° C. for 5 hours, the solvent was concentrated under reduced pressure to obtain a crude form of (1S,3R,4R)-3-amino-4-hydroxy-N,N-dimethylcyclohexanecarboxamide (1.18 g). The obtained crude form was dissolved in water (5 ml). To the solution, di-tert-butyl dicarbonate (1.93 g) and a 10 N aqueous sodium hydroxide solution (1.5 ml) were then added at room temperature. After stirring at 40° C. for 2 hours, the mixture was subjected to extraction with 4-methyl-2-pentanone (MIBK) (5 ml) three times, and the extraction solvent was distilled off under reduced pressure. To the residue, 4-methyl-2-pentanone (MIBK) (3 ml) was added, and the mixture was stirred at room temperature. The precipitated crystals were collected by filtration and then dried to obtain the title compound (1.26 g).

$^1$H-NMR (CDCl$_3$) δ: 1.44 (9H, s), 1.48-1.59 (2H, m), 1.77-1.78 (2H, m), 1.86-1.97 (1H, m), 2.11-2.17 (1H, m), 2.78-2.83 (1H, m), 2.92 (3H, s), 3.02 (3H, s), 3.53-3.60 (1H, m), 3.94 (1H, br.s), 4.52-4.68 (1H, m).

[Step 2] Synthesis of (1R,2R,4S)-2-[(tert-butoxycarbonyl)amino]-4-[(dimethylamino)carbonyl]cyclohexylmethanesulfonate (5)

(5)

wherein Ms represents a methanesulfonyl group; and Boc is as defined above.

Methanesulfonyl chloride (159.07 g) was added to a solution of tert-butyl {(1R,2R,5S)-5-[(dimethylamino)carbonyl]-2-hydroxycyclohexyl}carbamate (214.59 g) in 4-methyl-2-pentanone (MIBK) (1875 ml) at room temperature. To the reaction solution, triethylamine (170.62 g) was added at room temperature, and the mixture was stirred at this temperature for 1 hour. To the reaction solution, water was added, and then, the organic layer was separated. The solvent was concentrated under reduced pressure. Then, to the concentrated residue, MIBK (750 ml) was added, and the mixture was stirred at room temperature for 3 hours. The precipitated crystals were collected by filtration and dried to obtain the title compound (242.57 g).

$^1$H-NMR (CDCl$_3$) δ: 1.45 (9H, s), 1.58-1.66 (1H, m), 1.67-1.76 (1H, m), 1.84-1.96 (2H, m), 2.04-2.15 (1H, m), 2.17-2.26 (1H, m), 2.75-2.81 (1H, m), 2.94 (3H, s), 3.04 (3H, s), 3.07 (3H, s), 4.00-4.08 (1H, m), 4.69-4.82 (2H, m).

[Step 3] Synthesis of tert-butyl {(1R,2R,5S)-2-azido-5-[(dimethylamino)carbonyl]cyclohexyl}carbamate (6)

(6)

wherein Boc is as defined above.

Sodium azide (7.14 g) and dodecylpyridinium chloride (7.80 g) were added to a solution of (1R,2R,4S)-2-[(tert-butoxycarbonyl)amino]-4-[(dimethylamino)carbonyl]cyclohexylmethanesulfonate (20.0 g) in N,N-dimethylacetamide (DMAC) (40 ml) at room temperature. After stirring at 60° C. for 72 hours, water and ethyl acetate were added to the reaction solution. The organic layer was washed with a saturated aqueous solution of sodium bicarbonate and water, and then, the solvent was concentrated under reduced pressure. To the concentrated residue, an n-hexane-ethyl acetate (5:1) mixed solvent (300 ml) was added, and the mixture was stirred at room temperature for 1 hour. Crystals were collected by filtration. The procedure of adding an n-hexane-ethyl acetate (5:1) mixed solvent (300 ml) to the obtained crystals, followed by stirring and crystal collection by filtration was repeated twice to obtain the title compound (4.6 g).

$^1$H-NMR (CDCl$_3$) δ: 1.46 (9H, s), 1.55-1.74 (3H, m), 1.75-1.82 (1H, m), 2.02-2.12 (2H, m), 2.74-2.83 (1H, m), 2.93 (3H, s), 3.02 (3H, s), 3.72-3.78 (1H, m), 4.07-4.13 (1H, m), 4.61-4.66 (1H, m).

[Step 4] Synthesis of tert-butyl {(1R,2S,5S)-2-amino-5-[(dimethylamino)carbonyl]cyclohexyl}carbamate oxalate (3)

(3)

wherein Boc is as defined above.

Sodium azide (7.14 g) and dodecylpyridinium chloride (7.80 g) were added to a solution of (1R,2R,4S)-2-[(tert-butoxycarbonyl)amino]-4-[(dimethylamino)carbonyl]cyclohexylmethanesulfonate (20.0 g) in toluene (100 ml) at room temperature. The reaction mixture was stirred at 60° C. for 72 hours. To the reaction solution, water was then added, and the organic layer was washed with a saturated aqueous solution of sodium bicarbonate and water and then separated. To the organic layer, methanol, and then 7.5% Pd—C and ammonium formate were added, and the mixture was stirred at 40° C. for 1 hour. Pd—C was filtered off, and then, the solvent was concentrated under reduced pressure. To the residue, aqueous acetonitrile (200 ml) and anhydrous oxalic acid (4.94 g) were added, and the mixture was stirred at room temperature for 17 hours. Crystals were collected by filtration. The obtained crystals were added to acetonitrile (200 ml), and the mixture was stirred at 40° C. for 24 hours. The obtained crystals were collected by filtration and dried to obtain the title compound (12.7 g).

$^1$H-NMR (D$_2$O) δ: 1.30 (9H, s), 1.37-1.49 (2H, m), 1.63 (1H, t, J=2.7 Hz), 1.72-1.83 (3H, m), 2.77 (3H, s) 2.80 (1H, t, J=12.4 Hz), 2.96 (3H, m), 3.32 (1H, d, J=12.2 Hz), 4.10 (1H, br).

Reference Example 2

Ethyl 2-[(5-chloropyridin-2-yl)amino]-2-oxoacetate monohydrochloride (2)

(2)

Ethyl oxalyl chloride (2c) (11.7 g) was added to a suspension of 2-amino-5-chloropyridine (2b) (10.0 g) in acetonitrile (120 ml) at 50° C., and the mixture was stirred at this temperature for 2 hours. The reaction solution was cooled, and crystals were collected by filtration at 10° C., washed with acetonitrile (40 ml), and then dried under reduced pressure to obtain the title compound (2) (19.7 g).

Reference Example 3

Tert-butyl (1R,2S,5S)-2-({2-[(5-chloropyridin-2-yl)amino]-2-oxoacetyl}amino)-5-(dimethylaminocarbonyl)cyclohexylcarbamate (1)

(conventional process described in the pamphlet of International Publication No. WO 2007/032498 (JP 2007-106759))

(1)

wherein Boc is as defined above.

Triethylamine (169 ml) was added to a suspension of tert-butyl {(1R,2S,5S)-2-amino-5-[(dimethylamino)carbonyl]cyclohexyl}carbamate oxalate (1) (100.1 g) in acetonitrile (550 ml) at 60° C. Ethyl[5-chloropyridin-2-yl]amino] (oxo)acetate monohydrochloride (2) (84.2 g) was added thereto at this temperature, and the mixture was stirred for 6 hours and then stirred at room temperature for 16 hours. To the reaction solution, water was added, and the mixture was stirred at 10° C. for 1.5 hours. The deposited crystals were collected by filtration and dried to obtain the title compound (106.6 g, 85.4%).

$^1$H-NMR (CDCl$_3$) δ: 1.25-1.55 (2H, m), 1.45 (9H, s), 1.60-2.15 (5H, m), 2.56-2.74 (1H, br.s), 2.95 (3H, s), 3.06 (3H, s), 3.90-4.01 (1H, m), 4.18-4.27 (1H, m), 4.70-4.85 (0.7H, br), 5.70-6.00 (0.3H, br.s), 7.70 (1H, dd, J=8.8, 2.4 Hz), 7.75-8.00 (1H, br), 8.16 (1H, br.d, J=8.8 Hz), 8.30 (1H, d, J=2.4 Hz), 9.73 (1H, s).

Reference Example 4

N$^1$-(5-Chloropyridin-2-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide (A)

(A)

Methanesulfonic acid (66 ml) was added to a suspension of tert-butyl [(1R,2S,5S)-2-({[(5-chloropyridin-2-yl)amino](oxo)acetyl}amino)-5-(dimethylaminocarbonyl)cyclohexyl]carbamate (1) (95.1 g) in acetonitrile (1900 ml) at room temperature, and the mixture was stirred at this temperature for 2 hours. To the reaction solution, triethylamine (155 ml), 5-methyl-4,5,6,7-tetrahydro[1,3]thiazolo[5,4-c]pyridine-2-carboxylic acid hydrochloride (8) (52.5 g), 1-hydroxybenzotriazole (33.0 g), and 1-ethyl-3-(3-dimethylaminopropyl)carbodiimide hydrochloride (46.8 g) were added under ice cooling, and the mixture was stirred at room temperature for 16 hours. Triethylamine and water were added thereto, and the mixture was stirred for 1 hour under ice cooling. Then, crystals were collected by filtration to obtain the title compound (103.2 g).

$^1$H-NMR (CDCl$_3$) δ: 1.60-1.98 (3H, m), 2.00-2.16 (3H, m), 2.52 (3H, s), 2.78-2.90 (3H, m), 2.92-2.98 (2H, m), 2.95 (3H, s), 3.06 (3H, s), 3.69 (1H, d, J=15.4 Hz), 3.75 (1H, d, J=15.4 Hz), 4.07-4.15 (1H, m), 4.66-4.72 (1H, m), 7.40 (1H, dd, J=8.8, 0.6 Hz), 7.68 (1H, dd, J=8.8, 2.4 Hz), 8.03 (1H, d, J=7.8 Hz), 8.16 (1H, dd, J=8.8, 0.6 Hz), 8.30 (1H, dd, J=2.4, 0.6 Hz), 9.72 (1H, s).

MS (ESI) m/z: 548 (M+H)$^+$.

Reference Example 5

N$^1$-(5-Chloropyridin-2-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide mono-p-toluenesulfonate monohydrate (A-a)

(A-a)

N¹-(5-Chloropyridin-2-yl)-N²-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide (A) (6.2 g) was dissolved in methylene chloride (120 ml). To the solution, a 1 mol/L solution of p-toluenesulfonic acid in ethanol (11.28 ml) was added, and the mixture was stirred at room temperature. Then, the solvent was distilled off. To the residue, 15% hydrous ethanol (95 ml) was added, and the mixture was dissolved by stirring at 60° C. Then, the mixture was cooled to room temperature and stirred for 1 day. The precipitated crystals were collected by filtration, washed with ethanol, and then dried under reduced pressure at room temperature for 2 hours to obtain the title compound (7.4 g).

¹H-NMR (DMSO-$d_6$) δ: 1.45-1.54 (1H, m), 1.66-1.78 (3H, m), 2.03-2.10 (2H, m), 2.28 (3H, s), 2.79 (3H, s), 2.91-3.02 (1H, m), 2.93 (3H, s), 2.99 (3H, s), 3.13-3.24 (2H, m), 3.46-3.82 (2H, m), 3.98-4.04 (1H, m), 4.43-4.80 (3H, m), 7.11 (2H, d, J=7.8 Hz), 7.46 (2H, d, J=8.2 Hz), 8.01 (2H, d, J=1.8 Hz), 8.46 (1H, t, J=1.8 Hz), 8.75 (1H, d, J=6.9 Hz), 9.10-9.28 (1H, br), 10.18 (1H, br), 10.29 (1H, s).

MS (ESI) m/z: 548 (M+H)⁺.

Anal.: $C_{24}H_{30}ClN_7O_4S \cdot C_7H_8O_3S \cdot H_2O$

Theoretical: C; 50.43, H; 5.46, N; 13.28, Cl; 4.80, S; 8.69.

Found: C, 50.25; H, 5.36; N, 13.32; Cl, 4.93; S, 8.79.

mp (dec.): 245-248° C.

Example 1

Tert-butyl (1R,2S,5S)-2-({2-[(5-chloropyridin-2-yl)amino]-2-oxoacetyl}amino)-5-(dimethylaminocarbonyl)cyclohexylcarbamate (1)

wherein Boc represents a tert-butoxycarbonyl group.

2-Amino-5-chloropyridine (2b) (5.0 g) was added to acetonitrile (60 ml). Ethyl oxalyl chloride (2c) (5.9 g) was added thereto at 50° C., and the mixture was stirred at this temperature for 2 hours. The reaction solution was cooled, and crystals were collected by filtration at 10° C. to obtain ethyl[5-chloropyridin-2-yl]amino](oxo)acetate monohydrochloride (2) (9.8 g).

The ethyl[5-chloropyridin-2-yl]amino](oxo)acetate monohydrochloride (2) (8.48 g) thus obtained was suspended in acetonitrile (50 ml). To the suspension, triethylamine (3.17 g) was added at 10° C., and subsequently, tert-butyl {(1R,2S,5S)-2-amino-5-[(dimethylamino)carbonyl]cyclohexyl}carbamate oxalate (3) (10.0 g) was added thereto. Triethylamine (10.9 g) was added thereto at 60° C., and the mixture was stirred at 70° C. for 7 hours. The reaction solution was cooled, and water (90 ml) was added thereto. Crystals were collected by filtration at 10° C., washed with water (50 ml), and then dried under reduced pressure to obtain the title compound (1) (11.6 g).

Test Example 1

Reaction procedures were performed according to the conventional process described in Reference Example 3. The production yield of compound (1) in the solidified reaction system and the rate of formation of Impurity X* as by-product were evaluated and determined under (Condition 1) to (Condition 3) shown below. The results are shown in Table 1.

*Impurity X as by-product has a structure represented by the following formula:

(Condition 1): The conventional process shown in Reference Example 3 was performed under conditions in which the system was controlled to prevent solidification (controllable because of its small scale). Specifically, compound (3) (500 mg) was suspended in acetonitrile (2.5 ml). To the suspension, triethylamine (0.7 g) was added, and immediately thereafter, compound (2) (0.425 g) was quickly added. The temperature of the reaction mixture was raised to 75° C., and the mixture was stirred for 7 hours. The rate of formation of compound (1) under these conditions was defined as "1.0".

(Condition 2): Compound (3) (500 mg) was suspended in acetonitrile (2.5 ml). To the suspension, triethylamine (0.7 g) was added, and then, the mixed solution was left standing with its temperature set to 55° C. for 1 hour to solidify the system. After 1 hour, compound (2) (0.425 g) was added thereto. Then, the temperature of the reaction mixture was raised again to 75° C., and the mixture was stirred for 7 hours [the same as (Condition 1) except that the reaction system was solidified].

(Condition 3): Compound (3) (500 mg) was suspended in acetonitrile (2.5 ml). To the suspension, triethylamine (0.7 g), and subsequently compound (2) (0.425 g) were added, and then, the mixed solution was left standing with its internal temperature set to 55° C. for 1 hour to solidify the system. After 1 hour, the temperature of the reaction mixture was raised again to 75° C., and the mixture was stirred for 7 hours.

TABLE 1

| Condition | State of solidification | Rate of formation of compound (1) (Condition 1): 1.0 | Rate of formed Impurity X (%) |
|---|---|---|---|
| Condition 1 | Not solidified | 1.0 | 0.1 |
| Condition 2 | Heavily solidified before addition of compound (2) | 0.9 | 0.5 |
| Condition 3 | Solidified after addition of compound (2) | 0.99 | 0.1 |

HPLC conditions; Column: Shiseido CAPCELL PAK CN UG120 (4.6×250 mm); Detection: UV 254 nm; Column temperature: 40° C.; Flow rate: 1.0 ml/min.; Mobile phase: acetonitrile/0.02 M phosphate buffer (pH=7.0)=3/7.

<Test Results>

In the system solidified before the addition of compound (2) (Condition 2), the reduced rate of formation of compound (1) and the increased formation of Impurity X were observed based on poor stirring. In the system solidified after completion of the addition of compound (2) (Condition 3), such solidification had little influence on the yield of compound (1) and the rate of formation of Impurity X.

Test Example 2

The results of Test Example 1 demonstrated that the conventional process, which involved initially adding compound (3), has the risk of causing a reduction in quality of compound (1) (Condition 2 of Test Example 1). The rates of formation of compound (1) and Impurity X were determined under Condition 1 of Test Example 1 as well as (Condition 4) or (Condition 5) shown below for the purpose of confirming the influence of change in the order in which compound (3), compound (2), and triethylamine were added, on the yield and quality of compound (1). The results are shown in Table 2.

(Condition 4): Compound (3) (500 mg) and compound (2) (0.425 g) were suspended in acetonitrile (2.5 ml). To the suspension, triethylamine (0.7 g) was added with the internal temperature of the mixed solution set to 60° C. Then, the internal temperature of the reaction mixture was raised to 75° C., and the mixture was stirred for 7 hours.

(Condition 5): Compound (2) (0.425 g) was suspended in acetonitrile (2.5 ml). To the suspension, triethylamine (0.7 g) was added with the internal temperature of the mixed solution set to 60° C. Then, compound (3) (500 mg) was added thereto. The internal temperature of the reaction mixture was raised to 75° C., and the mixture was stirred for 7 hours (Example 2).

TABLE 2

| Condition | Rate of formation of compound (1) Condition 1: 1.0 | Rate of formation of Impurity X (%) |
|---|---|---|
| Condition 1 | 1.0 | 0.1 |
| Condition 4 | 0.75 | 15.9 |
| Condition 5 | 1.0 | <0.1 |

HPLC measurement value of a diluted solution of the whole amount after reaction; evaluated with the area % of compound (3) under current conditions defined as 100%; HPLC conditions; Column: Shiseido CAPCELL PAK CN UG120 (4.6×250 mm); Detection: UV 254 nm; Column temperature: 40° C.; Flow rate: 1.0 ml/min.; Mobile phase: acetonitrile/0.02 M phosphate buffer (pH=7.0)=3/7.

<Test Results>

When compound (3) and compound (2) were initially mixed and subsequently, triethylamine was added thereto as shown in (Condition 4), the rate of formation of Impurity X was drastically increased. This may be due to the elimination of the Boc group in compound (3). On the other hand, (Condition 5) resulted in high yields of compound (1) and a low rate of formation of Impurity X (Example 2), although some disadvantages were seen: an amorphous portion was observed in compound (3) due to the vapour of the added triethylamine; and fuming occurred along with the formation of hydrochloride of triethylamine and made compound (3) difficult to add. These test results demonstrated that a favorable yield and quality of compound (1) are obtained when compound (2) is initially added.

Test Example 3

The influence of the interval from completion of the addition of triethylamine (TEA) to initiation of the addition of compound (3) was investigated in detail under Condition 5 (Example 2) of Test Example 2. The results are shown in Table 3.

In the same way as in Condition 5 (Example 2) of Test Example 2, compound (2) (0.425 g) was suspended in acetonitrile (2.5 ml). To the suspension, triethylamine (0.7 g) was added with the internal temperature of the mixed solution set to 60° C. To the mixed solution, compound (3) (500 mg) was added under Conditions 5-1 to 5-5 (Examples 3 to 7) shown in Table 3. The internal temperature of the reaction mixture was further raised to 75° C., and the mixture was stirred for 7 hours. Then, the rates of formation of the compound (1) and Impurity X were determined.

TABLE 3

| Condition | Addition of compound (1) after addition of TEA | Rate of formation of compound (1) (%) | Impurity X (%) |
|---|---|---|---|
| 5-1 | Immediately after addition of TEA | 100 | <0.1 |
| 5-2 | Approximately 15 minutes after addition of TEA | 99 | <0.1 |
| 5-3 | Approximately 30 minutes after addition of TEA | 98 | <0.1 |
| 5-4 | Approximately 60 minutes after addition of TEA | 95 | <0.1 |
| 5-5 | Concurrently (after the point in time when the addition of ¼ of TEA was completed) | 100 | <0.1 |

HPLC measurement value of a diluted solution of the whole amount after reaction; evaluated with the area % of compound (1) under current conditions defined as 100%; HPLC conditions; Column: Shiseido CAPCELL PAK CN UG120 (4.6×250 mm); Detection: UV 254 nm; Column temperature: 40° C.; Flow rate: 1.0 ml/min.; Mobile phase: acetonitrile/0.02 M phosphate buffer (pH=7.0)=3/7.

<Test Results>

The longer the interval from completion of the addition of triethylamine to initiation of the addition of compound (3) was, the more largely the rate of formation of compound (1) was reduced.

Test Example 4

2-[(5-Chloropyridin-2-yl)amino]-2-oxoacetate (2a) (free form of compound (2)) was tested for its stability. To compound (2), triethylamine was added at 4.3 molar equivalents with respect to compound (2), and then, the time-dependent residual rate of compound (2a) was determined at 45° C., 55° C., 65° C., and 75° C. The results are shown in FIG. 1.

<Test Results>

Figure 1:
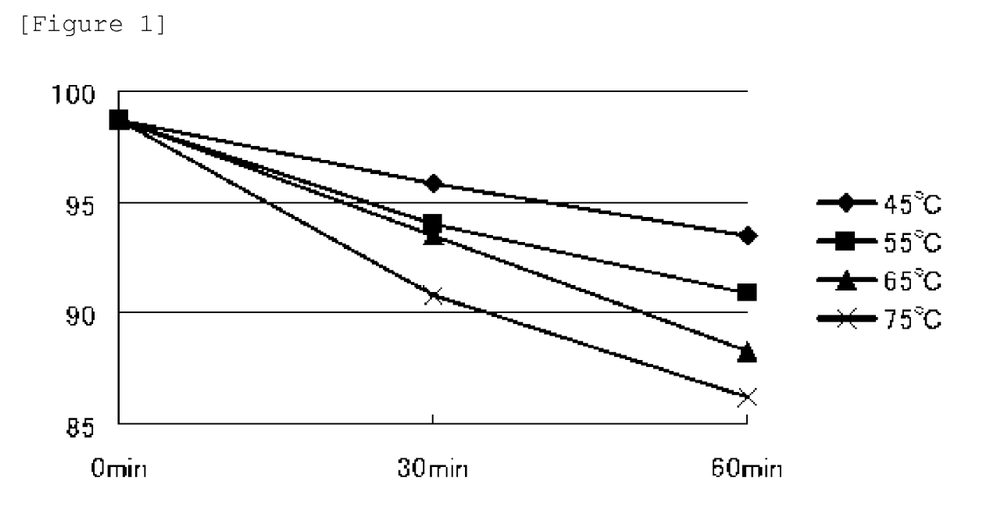
FIG. 1 is a diagram showing the time-dependent residual rate of 2-[(5-chloropyridin-2-yl)amino]-2-oxoacetate ((2a); free form of compound (2)) exposed to 45° C., 55° C., 65° C., or 75° C. after addition of triethylamine at 4.3 molar equivalents with respect to compound (2) to confirm the stability of compound (2a).

As shown in FIG. 1, in the presence of a great excess of triethylamine, the residual rate of compound (2a) was decreased with an increase in temperature. This result suggests that the decomposition of compound (2a) is influenced by the presence of an excessive amount of triethylamine and the temperature.

Test Example 5

Based on the results of Test Example 4 showing that the presence of a great excess of triethylamine promoted the decomposition of compound (2a), compound (2a) was evaluated for its stability by decreasing the amount of triethylamine added.

Figure 2:
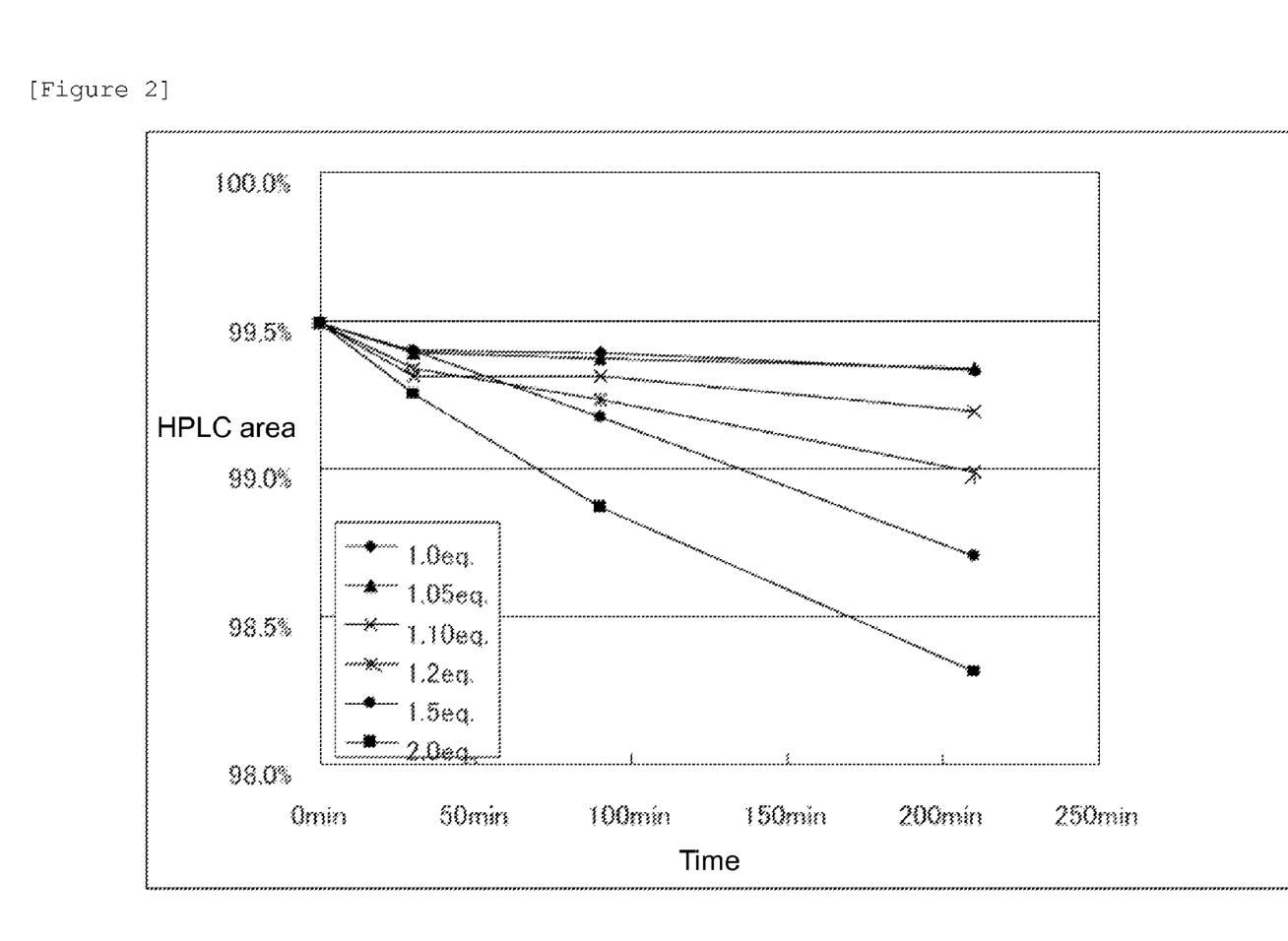
FIG. 2 is a diagram showing the time-dependent residual rate of 2-[(5-chloropyridin-2-yl)amino]-2-oxoacetate ((2a); free form of compound (2)) exposed to 60° C. after addition of compound (2) (500 mg) to acetonitrile (3 ml) and addition of triethylamine at 1 to 2 molar equivalents with respect to compound (2) to confirm the stability of compound (2a).

To compound (2) (500 mg), acetonitrile (3 ml) was added, and triethylamine was added thereto in a range of stoichiometrically 1 to 2 molar equivalents with respect to compound (2). The residual rate of compound (2a) was determined at 60° C. The results are shown in FIG. 2.

<Test Results>

When triethylamine was added at 1.5 molar equivalents, only approximately 0.3% of compound (2a) was decomposed per 1 hour. This demonstrated that the decomposition of compound (2a) seen in Test Example 4 can be avoided by decreasing the amount of triethylamine added.

Test Example 6

It was demonstrated that the decomposition of compound (2a) can be avoided by the amount of triethylamine added. Next, whether the system was solidified by adding triethylamine at 1.07 to 1.15 molar equivalents to compound (2) and further adding compound (3) was evaluated under Conditions 6 and 7 (Examples 8 and 9) and Condition 8 (Comparative Example).

Compound (2) (8.5 g) was added to acetonitrile (50 ml), and triethylamine shown in Table 4 was added thereto with stirring at 10° C. After completion of the addition, compound (3) (10 g) was added thereto, and the flowability of the system was tested by visual observation.

TABLE 4

| Condition | First amount of triethylamine added (vs. molar equivalent of compound (2)) | Stirring flowability |
|---|---|---|
| 6 | 1.07 parts by molar weight | ○ |
| 7 | 1.10 parts by molar weight | Δ |
| 8 | 1.15 parts by molar weight | x |

<Test Results>

The results demonstrated that as long as triethylamine is added at 1.10 molar equivalents or less, the system is not solidified even after addition of compound (3) and can be stirred without problems. Moreover, when triethylamine was added at low temperatures, only slight fuming occurred and no amorphous portion attributed to the vapour of triethylamine was observed in compound (3).

Test Example 7

The rates of formation of compound (1) and Impurity X obtained by adding triethylamine in divided portions and the presence or absence of heavy fuming caused by the addition of triethylamine were tested under Condition 9 (Comparative Example) and Conditions 10 to 12 (Examples 10 to 12).

Compound (2) (8.5 g) was added to acetonitrile (50 ml), and triethylamine was added thereto in a first amount shown in Table 5 with stirring at 10° C. After completion of the addition, the compound (3) (10 g) was added thereto, and then, triethylamine was added in a second amount at 60° C. (total amount of triethylamines: 5.2 molar equivalents with respect to compound (2)).

TABLE 5

| Condition | First amount of TEA (vs. molar equivalent of compound (2)) | Total amount of TEA (vs. molar equivalent of compound (2)) | Yield of compound (1) (%) | Impurity X (%) | Heavy fuming caused by addition of TEA |
|---|---|---|---|---|---|
| 9 | None | 5.2 | 93.8 | 0.02 | Present |
| 10 | 0.87 | 5.2 | 94.7 | 0.04 | Absent |
| 11 | 0.98 | 5.2 | 93.5 | 0.02 | Absent |
| 12 | 1.08 | 5.2 | 94.6 | 0.02 | Absent |

<Test Results>

Even when triethylamine was added in divided portions, the yield and quality of the compound (1) were favorable.

Industrial Applicability

The production process of the present invention can be used as a novel process for industrially producing compound (A) useful as an FXa inhibitor or a pharmacologically acceptable salt thereof, or a hydrate thereof.

The invention claimed is:

1. A process for producing a compound (1) represented by the following formula:

(1)

wherein Boc represents a tert-butoxycarbonyl group, the process comprising:

(i) treating a compound (2) represented by the following formula:

(2)

with a tertiary amine in a C2-C4 nitrile solvent; and
(ii) then adding, to the mixed solution of step (i), a compound (3) represented by the following formula:

wherein Boc is as defined above.

2. The production process according to claim 1, wherein the C2-C4 nitrile solvent is acetonitrile.

3. The production process according to claim 1, wherein the amount of compound (2) is stoichiometrically 1.10 to 1.27 molar equivalents with respect to compound (3).

4. The production process according to claim 1, wherein the tertiary amine is one or two or more selected from the group consisting of tri(C1-C4 alkyl)amines, 1-(C1-C3alkyl) piperidine, and 4-(C1-C3 alkyl)morpholine.

5. The production process according to claim 1, wherein the tertiary amine is one or two or more selected from tri(C1-C4 alkyl)amines.

6. The production process according to claim 1, wherein the tertiary amine is triethylamine.

7. The production process according to claim 1, wherein step (i) comprises adding compound (2) represented by the following formula:

into the C2-C4 nitrile solvent and subsequently adding the tertiary amine thereto.

8. The production process according to claim 1, wherein step (i) comprises adding the tertiary amine into the C2-C4 nitrile solvent and subsequently adding thereto compound (2) represented by the following formula:

9. The production process according to claim 7, wherein the addition of compound (2) or the tertiary amine is performed at 45° C. or lower.

10. The production process according to claim 7, wherein the addition of compound (2) or the tertiary amine is performed in the range of 0 to 35° C.

11. The production process according to claim 1, wherein the amount of the tertiary amine added in step (i) is stoichiometrically 0.87 to 1.08 molar equivalents with respect to compound (2).

12. The production process according to claim 1, further comprising adding an additional tertiary amine after the procedure of step (ii).

13. The production process according to claim 12, wherein the amount of the additional tertiary amine added is stoichiometrically in the range of 3.02 to 4.53 molar equivalents with respect to compound (2).

14. The production process according to claim 12, wherein the addition of the additional tertiary amine is performed at 50 to 65° C.

15. The production process according to claim 12, further comprising stirring the reaction mixture at 60 to 80° C. after the addition of the additional tertiary amine.

16. The production process according to claim 15, wherein the stirring time is 6 hours or longer.

17. The production process according to claim 15, wherein the stirring time is in the range of 6 to 24 hours.

18. A process for producing a compound (1) represented by the following formula:

wherein Boc represents a tert-butoxycarbonyl group, the process comprising:
(i) treating a compound (2) represented by the following formula:

with triethylamine at stoichiometrically 0.87 to 1.08 molar equivalents with respect to compound (2) in acetonitrile;
(ii) then adding, to the mixed solution of step (i), a compound (3) represented by the following formula:

wherein Boc is as defined above,
(iii) then adding an additional tertiary amine at stoichiometrically 3.23 to 4.32 molar equivalents with respect to compound (2) at 50 to 65° C., and
(iv) stirring the reaction mixture at 60 to 80° C. for 6 hours or longer.

* * * * *